US012268382B2

(12) United States Patent
Börner et al.

(10) Patent No.: US 12,268,382 B2
(45) Date of Patent: Apr. 8, 2025

(54) CRIMPING DEVICE AND METHOD

(71) Applicant: Suturion AB, Ramlösa (SE)

(72) Inventors: Gabriel Börner, Ramlösa (SE); Eskil Reimhagen, Malmö (SE); Mikael Skoglund, Stehag (SE); Rickard Norenstam, Löddeköpinge (SE)

(73) Assignee: Suturion AB, Ramlösa (SE)

( * ) Notice: Subject to any disclaimer, the term of this patent is extended or adjusted under 35 U.S.C. 154(b) by 931 days.

(21) Appl. No.: 17/341,665

(22) Filed: Jun. 8, 2021

(65) Prior Publication Data
US 2021/0378660 A1   Dec. 9, 2021

(30) Foreign Application Priority Data

Jun. 8, 2020  (EP) ..................................... 20178675

(51) Int. Cl.
| | | |
|---|---|---|
| *A61B 17/04* | (2006.01) | |
| *B25B 27/02* | (2006.01) | |
| *B23P 19/02* | (2006.01) | |

(52) U.S. Cl.
CPC .. *A61B 17/0469* (2013.01); *A61B 2017/0472* (2013.01); *B23P 19/02* (2013.01); *B25B 27/02* (2013.01)

(58) Field of Classification Search
CPC ... A61B 17/06004; B23P 19/02; B25B 27/02; H01R 43/042; Y10T 29/53235; Y10T 29/53226; Y10T 29/53996; Y10T 29/53987
See application file for complete search history.

(56) References Cited

U.S. PATENT DOCUMENTS

| | | | |
|---|---|---|---|
| 3,879,981 A * | 4/1975 | Richards | H01R 43/042 |
| | | | 72/415 |
| 4,932,962 A | 6/1990 | Yoon et al. | |
| 5,428,983 A * | 7/1995 | Liu | H01R 43/042 |
| | | | 72/409.13 |
| 6,120,527 A | 9/2000 | Richard et al. | |
| 6,604,403 B1 * | 8/2003 | Eslambolchi | H01R 43/042 |
| | | | 29/282 |
| 6,877,352 B1 | 4/2005 | Schlereth | |
| 8,826,958 B2 | 9/2014 | Matsutani et al. | |
| 2020/0078006 A1 | 3/2020 | Moretti et al. | |

FOREIGN PATENT DOCUMENTS

| | | |
|---|---|---|
| WO | 2005/069743 A2 | 8/2005 |
| WO | 2010/054431 A1 | 5/2010 |

* cited by examiner

*Primary Examiner* — Tyrone V Hall, Jr.
(74) *Attorney, Agent, or Firm* — DINSMORE & SHOHL LLP (57) ABSTRACT

A crimping device for securing a suture to a double-pointed medical suture needle includes a lower block and an upper block that can be pressed against each other to secure the suture to the double-pointed medical suture needle. Each of the lower block and upper block have a first groove configured to accommodate the suture; and a second groove configured to accommodate the double-pointed medical suture needle, the second groove extending in a second groove extension substantially perpendicular to a first groove extension of the first groove, wherein the second groove comprises a protrusion at an intercept of the first groove and second groove. The disclosure further relates to a method of securing at least one suture to at least one double-pointed medical suture needle.

17 Claims, 7 Drawing Sheets

CRIMPING DEVICE AND METHOD

FIELD OF THE INVENTION

The present disclosure relates to a method and a crimping device for securing a suture to a double-pointed medical suture needle.

BACKGROUND

Surgical needles come in a number of variants and are used for a number of purposes, ranging from simple closure of wounds to advanced surgery.

Eyed needles, which are often reusable and supplied separate from their suture thread, are often used for suturing. The suture must be threaded on site, which is a time-consuming task. One advantage, however, is that a number of different thread and needle combinations are possible.

A swaged needle is typically supplied as a pre-packed eyeless needle attached to a specific length of suture thread. One advantage of this is that the medical staff does not have to spend time on threading the suture on the needle. A further advantage is that the needle end and suture are joined as a continuous unit, which minimizes trauma to tissue during suturing. A swaged needle may have one pointed end and one hollow end, in which the suture is placed and secured.

In some surgical procedures, for example, open surgical procedures, the wound may be closed using a suturing device with built-in needle-transfer of a double-pointed needle. In these devices, a double-pointed needle is transferred between two jaws, preferably in an automatic fashion by opening and closing the jaws repeatedly, to close the wound.

The process of crimping the suture to the needle requires precision both in terms how much pressure is applied and where the pressure is applied. There is thus a need for a precise, efficient, reliable and fast tool for fastening a suture to a needle.

SUMMARY

The present disclosure relates to a method and a crimping device for securing a suture to a medical suture needle. The medical suture needle is, preferably, of a type having to pointed ends and a needle body having a through-hole for the suture. A first embodiment of the presently disclosed crimping device for securing a suture to a double-pointed medical suture needle comprises:

a lower block and an upper block that can be pressed against each other to secure the suture to the double-pointed medical suture needle, each of the lower block and upper block comprising:

a. a first groove configured to accommodate the suture; and b. a second groove configured to accommodate the double-pointed medical suture needle, the first and second grooves arranged substantially perpendicularly to each other, wherein the second groove comprises a protrusion at an intercept of the first groove and second groove.

Figure 2:
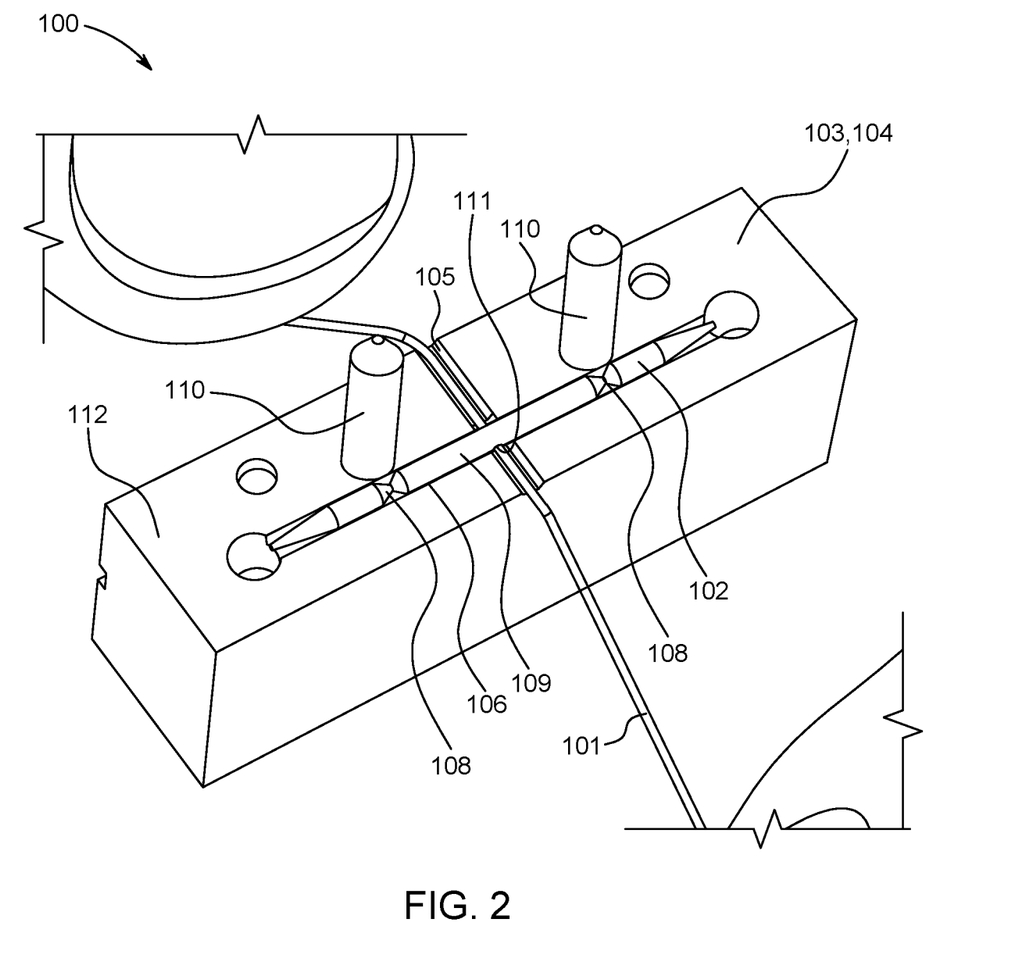
FIG. 2 is a perspective view of an embodiment of a lower block in which a double-pointed medical suture needle and suture have been placed for crimping.

Preferably, the double-pointed medical suture needle is threaded before the needle and suture is placed in one of the upper and lower blocks, for example, the lower block. FIG. 2 shows an example of a lower block, wherein the double-pointed medical suture needle and the suture are arranged in the block and ready to be crimped.

The second groove comprises a protrusion at an intercept of the first groove and second groove. When the lower block and the upper block are pressed against each other, the protrusions cause a deformation of the double-pointed medical suture needle, preferably from two opposite sides of the double-pointed medical suture needle. The deformation bonds the suture to the double-pointed medical suture needle, which can then be cut and packaged.

The double-pointed medical suture needle used in, for example, suturing devices with built-in needle-transfer of the needle between two jaws may have two indentations, which may be used to hold the needle. The double-pointed medical suture needle does not have to be limited to any specific number of indentations, and may have further indentations, such as 3, 4, 5, 6, 7, 8, 10, 12 or 16 indentations. The inventors have realized that these indentations can be used to lock the double-pointed medical suture needle in a position such that the protrusions deform the double-pointed medical suture needle exactly at the through-hole for the suture.

The inventors have found that the presently disclosed crimping device for securing a suture to a double-pointed medical suture needle provides an efficient, reliable and fast tool for fastening a suture to a needle. By using the device the double-pointed medical suture needles can be supplied as a pre-packed needles for, for example, an automated or semi-automated disposable suturing device.

The present disclosure further relates to a method of securing at least one suture to at least one double-pointed medical suture needle, comprising the steps of:

threading the double-pointed medical suture needle by inserting the suture through a through-hole of the double-pointed medical suture needle;

providing a crimping device according to the present disclosure;

placing the double-pointed medical suture needle in a second groove and the suture in the first groove of the crimping device; and crimping the double-pointed medical suture needle by pressing the lower block and the upper block of the crimping device together, thereby securing the suture to the double-pointed medical suture needle.

The method may further comprise the step of locking the double-pointed medical suture needle by engaging one or more locking elements with one or more indentations of the double-pointed medical suture needle such that the through-hole is aligned with the intercept.

A person skilled in the art will recognize that the presently disclosed method of securing a suture to a double-pointed medical suture needle may be performed using any embodiment of the presently disclosed crimping device for securing a suture to a double-pointed medical suture needle.

DETAILED DESCRIPTION

The present disclosure relates to crimping device for securing a suture to a double-pointed medical suture needle. The crimping device comprises a lower block and an upper block that can be pressed against each other to secure the suture to the double-pointed medical suture needle. Each of the blocks comprise one groove configured to accommodate the double-pointed medical suture needle, and, preferably, one groove configured to accommodate the suture. The groove for accommodating the suture may be referred to as the first groove, and the groove for accommodating the double-pointed medical suture needle may be referred to as the second groove. The second groove may comprise a protrusion, which is preferably located at an intercept of the first groove and second groove. Preferably, the extension of the first and second grooves are substantially perpendicular. Hence, the second groove may extend in a second groove extension which is substantially perpendicular to a first groove extension of the first groove. The entire first groove may not have to be substantially perpendicularly arranged with respect to the second groove. However, it is an advantage that at least a section of the first groove adjacent to the intercept of the first groove and second groove is arranged substantially perpendicularly arranged with respect to the second groove.

The presently disclosed crimping device for securing a suture to a double-pointed medical suture needle provides an efficient, reliable and fast tool for fastening a suture to a needle, which can be used as part of manufacturing process with the aim of supplying pre-packed double-pointed medical suture needles with a suture attached.

The inventors have realized that double-pointed medical suture needles, in particular double-pointed medical suture needles having a through-hole in the needle body for the suture, are associated with challenges related to the attachment of the suture, in particular attachment on an industrial scale. The inventors have therefore developed a crimping device that can secure a suture to a double-pointed medical suture needle efficiently wherein the alignment of the part that deforms the needle and the needle is built into the device.

Figure 5:
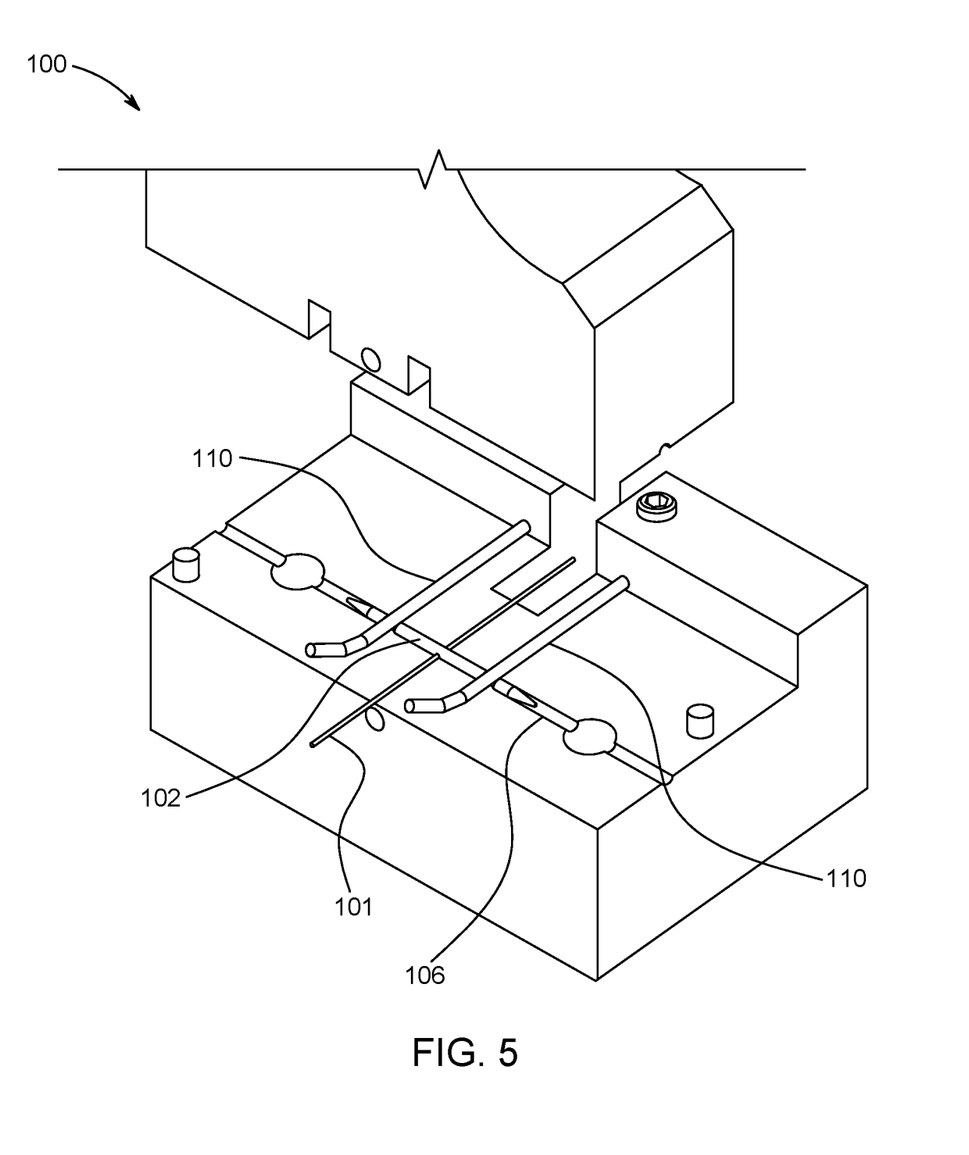
FIG. 5 is a perspective view showing a further embodiment of the presently disclosed crimping device.

Double-pointed medical suture needles used in, for example, suturing devices with built-in needle-transfer of the needle between two jaws, may have two indentations, which may be used by the presently disclosed suturing device to hold the needle. The double-pointed medical suture needle does not have to be limited to any specific number of indentations, and may have further indentations, such as 3, 4, 5, 6, 7, 8, 10, 12 or 16 indentations. These indentations may be used to further improve the alignment between the area of the double-pointed medical suture needle to be crimped, i.e. an area located at the through-hole, and the crimping device. The crimping device may comprise one or more locking elements, such as two locking elements, such as two rods, configured to engage with the two indentations in a locked position such that the through-hole is aligned with the intercept, which also means that the area of the double-pointed medical suture needle to be crimped is aligned with the protrusion. The locking element(s) may, for example, be disposed on a lower block needle facing surface to lock the double-pointed medical suture needle against the lower block in the locked position, as shown in FIG. 5. In this embodiment the upper block may comprise corresponding locking element receiving grooves for receiving the locking elements in the locked position. Alternatively, locking element(s) may be arranged substantially perpendicularly to a lower block needle facing surface towards the upper block, wherein the locking element(s) partly interfere with the second groove. Such an embodiment is shown in FIG. 2. The upper block may comprise guiding holes for receiving the locking elements.

The protrusion in the second groove has the purpose of deforming the double-pointed medical suture needle at the through-hole when the lower and upper blocks are pressed together. Technically, the protrusion may, according to some embodiments, be disposed in the first groove. However, in order to cause a deformation of the double-pointed medical suture needle, which is accommodated in the second groove, the protrusion would then have to be disposed at the intersect of the first and second grooves. The protrusion may take any shape that is suitable for deforming the double-pointed medical suture needle. In one embodiment, the protrusion has the shape of a bulge or a straight or curved hump. The protrusion may, alternatively, or, in combination, have a contour towards the double-pointed medical suture needle that has the shape of a tooth of a cog-wheel, pointed (single or multi pointed), substantially pyramid shaped, U-shaped (bottom part of the 'U' facing the needle). As a person skilled in the art would recognize, the contact area between the protrusion and can be adapted to specific needle and suture sizes dimensions, including the dimensions of the trough-hole. As can be realized form FIG. 4, which shows a cross-section of an embodiment of one block, the protrusion will cause a deformation of a needle placed in the second groove if the block is pressed against another block. Material of the needle, for example metal, will then be pressed into the through-hole, which will be reduced in size and which will eventually firmly hold the suture. The protrusions may thus be configured to cause a deformation of the double-pointed medical suture needle to bond the suture to the double-pointed medical suture needle when the lower block and the upper block are pressed against each other. According to one embodiment of the presently disclosed crimping device for securing a suture to a double-pointed medical suture needle, the protrusions are configured to cause a deformation of the double-pointed medical suture needle from two opposite sides.

Figure 4:
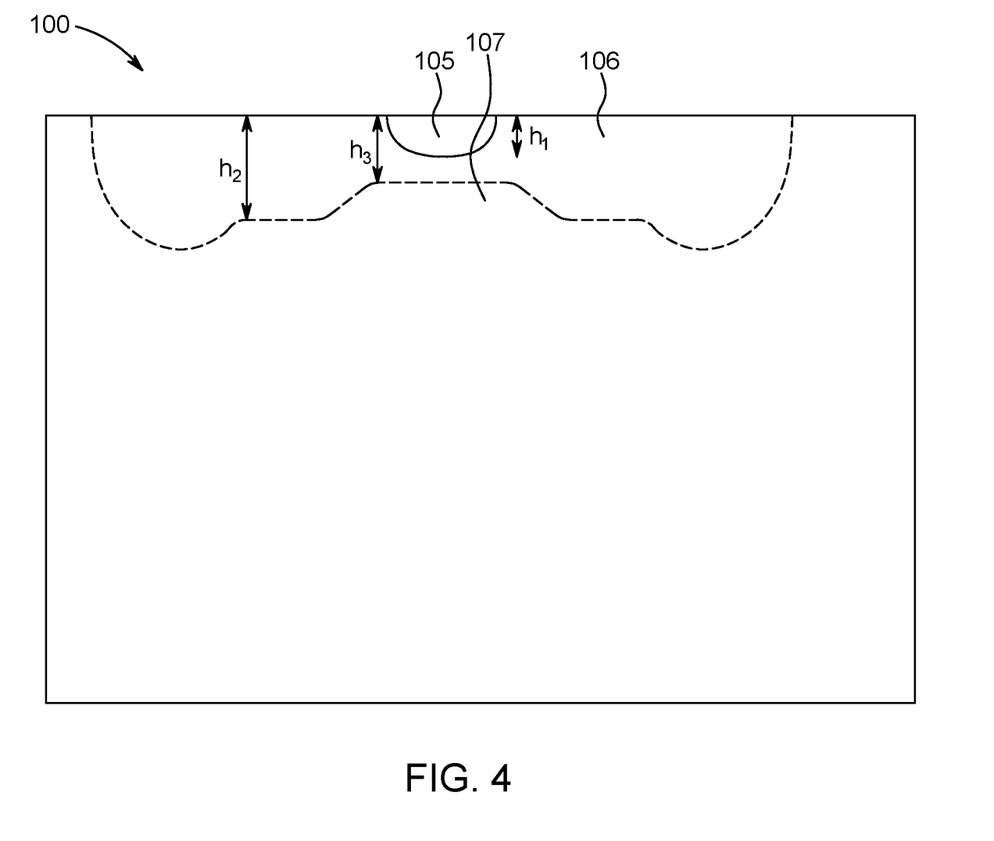
FIG. 4 is a cross-sectional view of one of the lower block and upper block.

The first groove and second groove may be arranged such that the first groove has a first height and the second groove has a second height, wherein the second height is greater than the first height. An example of this is shown in FIG. 4. The second height $h_2$ may correspond to approximately the needle radius of the double-pointed medical suture needle to be crimped. The first height $h_1$ may correspond to approximately the radius of the suture to be secured to the double-pointed medical suture needle. The second groove may have a third height at the protrusion, wherein the third height is greater than the first height and less than the second height. The third height is what causes the deformation of the needle. The double-pointed medical suture needle may be made of any suitable material, typically a metal or metal alloy, such as stainless steel.

According to one embodiment of the presently disclosed crimping device for securing a suture to a double-pointed medical suture needle, the second groove is substantially straight. The first groove may also be substantially straight.

Figure 1:
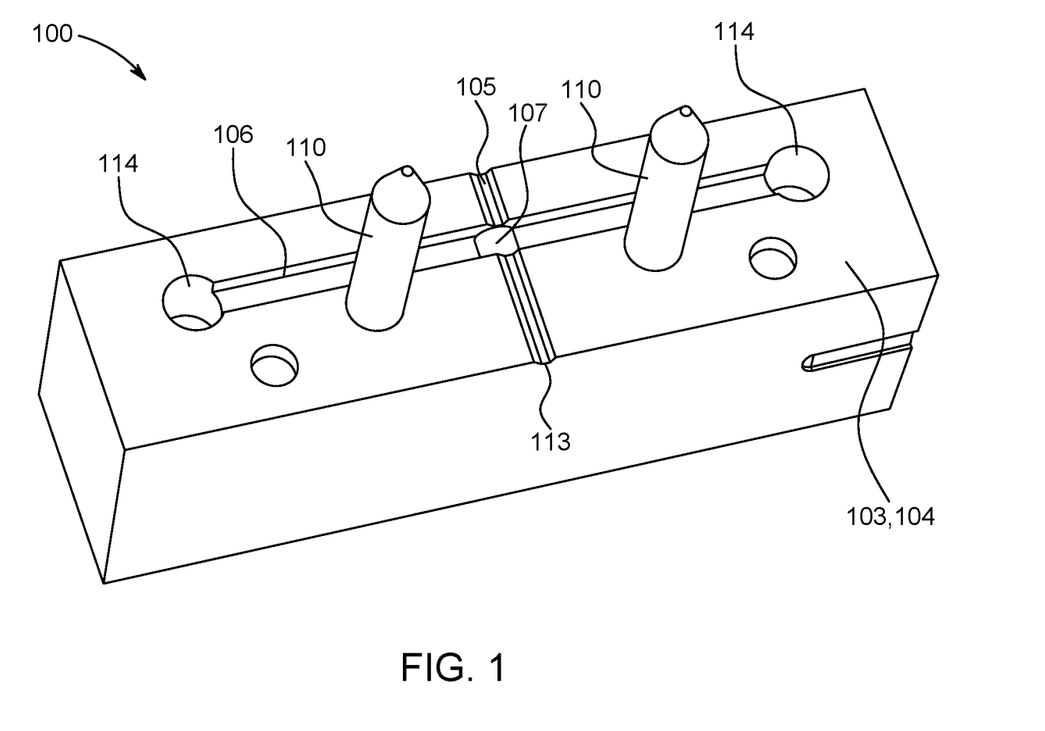
FIG. 1 is a perspective view of an embodiment of a lower block.
Figure 8:
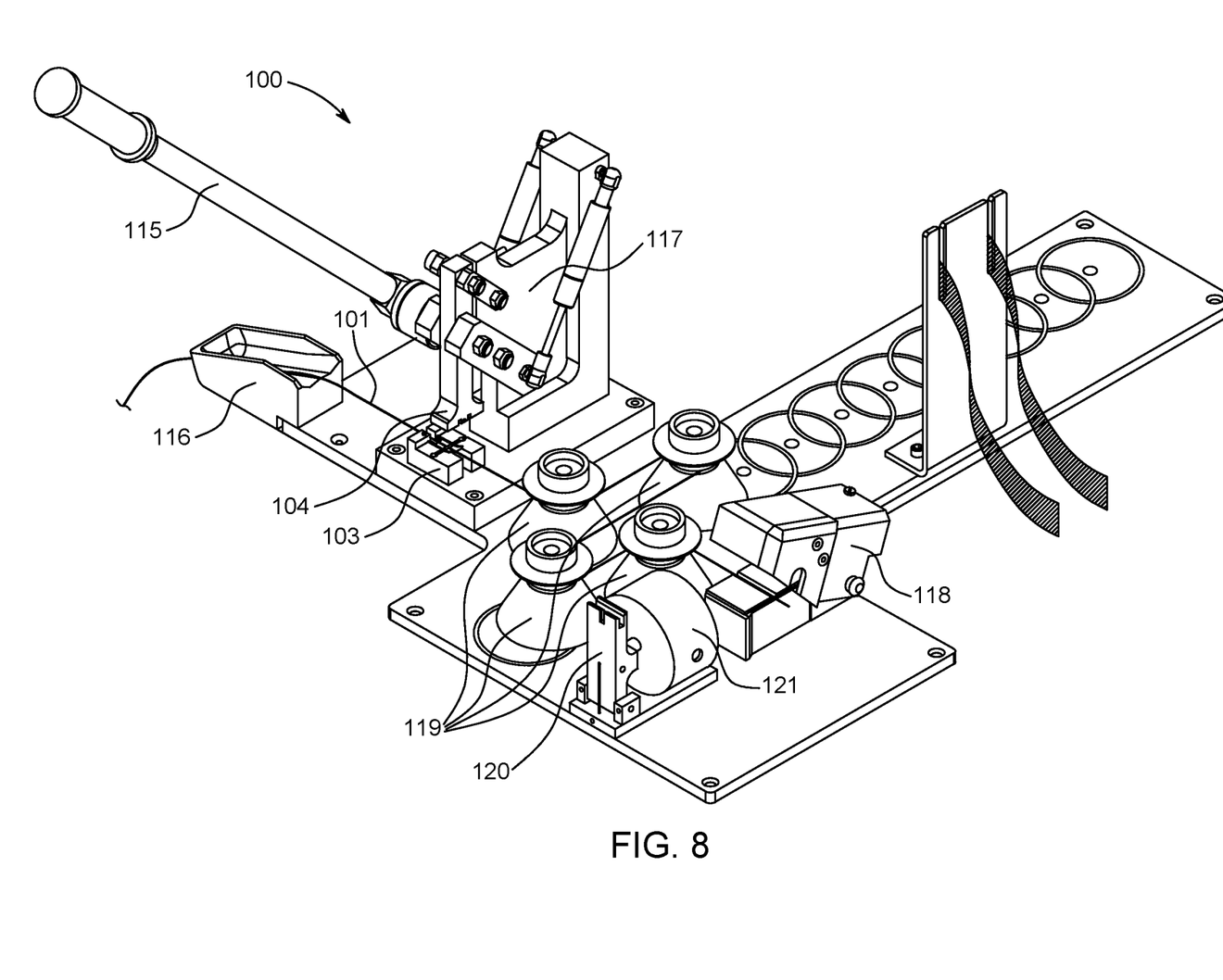
FIG. 8 is a perspective view of an embodiment of the presently disclosed crimping device comprising suture length adjustment elements and cutting mechanisms.

The lower block and the upper block have suture side openings for the suture, as shown in, for example FIG. 1. One advantage of having these openings is that one long suture can be threaded through many double-pointed medical suture needles in a crimping process for a plurality of double-pointed medical suture needles. The needles can then be crimped one by one in the crimping device. When a needle has been crimped it can move on to a suture length adjustment and cutting procedure, as shown in FIG. 8. The crimping device may hence further comprise a cutting mechanism for cutting the suture and/or a suture length adjustment elements and/or a winding mechanism for winding the suture.

The lower block and the upper block may also have needle side openings for the double-pointed medical suture needle. Alternatively, or in combination, the lower block and the upper block may comprise a free space around each pointed end of the double-pointed medical suture needle. The free space may be a substantially spherical space or any other suitable shape.

The present disclosure further relates to a method of securing at least one suture to at least one double-pointed medical suture needle, comprising the steps of:
 threading the double-pointed medical suture needle by inserting the suture through a through-hole of the double-pointed medical suture needle;
 providing a crimping device having a lower block and an upper block, each of the lower block and the upper block comprising a first groove configured to accommodate the suture; and
 a second groove configured to accommodate the double-pointed medical suture needle, the second groove extending in a second groove extension substantially perpendicular to a first groove extension of the first groove, wherein the second groove comprises a protrusion at an intercept of the first groove and second groove;
 placing the double-pointed medical suture needle in the second groove and the suture in the first groove; and
 crimping the double-pointed medical suture needle by pressing the lower block and the upper block together, thereby securing the suture to the double-pointed medical suture needle.

The method may be performed using any embodiment of the presently disclosed crimping device for securing a suture to a double-pointed medical suture needle.

Preferably, the protrusion of each of the second groove deform the double-pointed medical suture needle at the through-hole in the step of crimping the double-pointed medical suture needle. The method may further comprise the step of cutting the suture, adjusting the suture length and/or winding the suture.

The method may also operate in a serial crimping procedure of a plurality of double-pointed medical suture needles. In this procedure the plurality of double-pointed medical suture needles may be threaded using the same suture, wherein the double-pointed medical suture needles are crimped one by one, and wherein the suture is winded and cut for each crimping.

DETAILED DESCRIPTION OF THE DRAWINGS

The invention will in the following be described in greater detail with reference to the accompanying drawings. The drawings are exemplary and are intended to illustrate some of the features of the presently disclosed method and a crimping device for securing a suture to a double-pointed medical suture needle, and are not to be construed as limiting to the presently disclosed invention.

FIG. 1 shows an embodiment of a lower block (103) or an upper block (104) of the presently disclosed crimping device (100) (the crimping device comprises both a lower block and an upper block). The block (103, 104) has a first groove (105) for accommodating a suture and a second groove (106) for accommodating a double-pointed medical suture needle. The second groove (106) has a protrusion (107) at the intercept of the first groove (105) and second groove (106). The block (103, 104) further comprises two locking elements (110). In this embodiment the two locking elements (110) configured to engage with two indentations of the needle (not shown) in a locked position such that the through-hole of the needle is aligned with the intercept of the first groove (105) and second groove (106). In this embodiment the locking elements also are arranged to fit two corresponding guiding holes for receiving the two locking elements. The block (103, 104) further comprises suture side openings (113) for the suture and a free space (114) around each pointed end of the double-pointed medical suture needle.

FIG. 2 shows an embodiment of a lower block (103) or an upper block (104) of the presently disclosed crimping device (100), in which a double-pointed medical suture needle (102) and suture (101) have been placed for crimping. The block (103, 104) has a first groove (105) in which a suture (101) is accommodated and a second groove (106) in which a double-pointed medical suture needle (102) is accommodated. The double-pointed medical suture needle (102) is thereby in a crimping configuration. The second groove (106) has a protrusion (not visible) at the intercept of the first groove (105) and second groove (106). A through-hole (111) of the double-pointed medical suture needle (102) is also located at the intercept of the first groove (105) and second groove (106) in the crimping configuration. The block (103, 104) has a needle facing surface (112). If the block (103, 104) is pressed against a corresponding upper/lower block, i.e. the needle facing surfaces (112) are pressed against each other, the protrusion (not visible) will deform the double-pointed medical suture needle (102) at the through-hole (111) to bond the suture (101) to the double-pointed medical suture needle (102). The block (103, 104) further comprises two locking elements (110).

Figure 3:
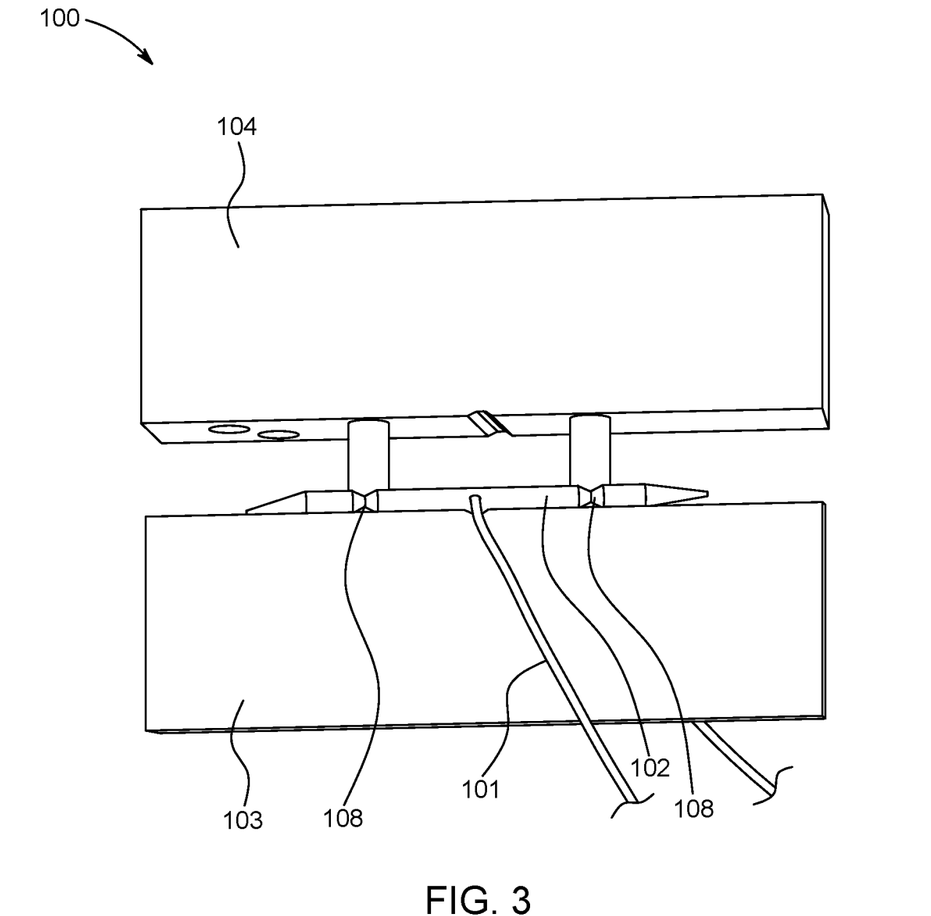
FIG. 3 is a perspective view showing an example of a the presently disclosed crimping device in a configuration wherein the lower and upper blocks are not pressed against each other.

FIG. 3 shows an embodiment of the presently disclosed crimping device (100) in a configuration wherein the lower (103) and upper block (104) are not pressed against each other. If the blocks (103, 104) are pressed against each other the protrusion (107) in the second grove (106) will deform the double-pointed medical suture needle (102) at the through-hole (111) to bond the suture (101) to the double-pointed medical suture needle (102).

FIG. 4 shows a cross-section of an embodiment of one of the lower block (103) and upper block (104). The profile of the second groove (106), which extends from the left to the right in the figure, has a profile wherein a main part having a second height or radius $h_2$. The second height $h_2$ may correspond to approximately half of the diameter of the double-pointed medical suture needle (102) to be crimped. The protrusion (107) makes the height or radius of the groove smaller (narrower groove) at a section corresponding to the area of the double-pointed medical suture needle (102) to be crimped. This height or radius may be referred to as the third height $h_3$. The cross-section of FIG. 4 is from the intercept of the first groove (105) and second groove (106). The first groove (105) has a first height or radius h.sub.1, which is smaller than both h.sub.2 and h.sub.3. When the lower block (103) and upper block (104) are pressed against each other, the double-pointed medical suture needle (102) may be deformed to have a contour substantially following the contour of the second groove (106). This means that a substantially cylindrical double-pointed medical suture needle (102) will be deformed at the intercept in a way that metal will be pressed into through-hole (111) of the a double-pointed medical suture needle (102), which may substantially coincide with the first groove (105) before the crimping.

FIG. 5 shows a further embodiment of the presently disclosed crimping device (100). In this embodiment the locking elements (110) are disposed on a lower block needle facing surface (112) to lock the double-pointed medical suture needle (102) against the lower block in a locked position by engage with the two indentations (108) of the double-pointed medical suture needle (102).

Figure 6:
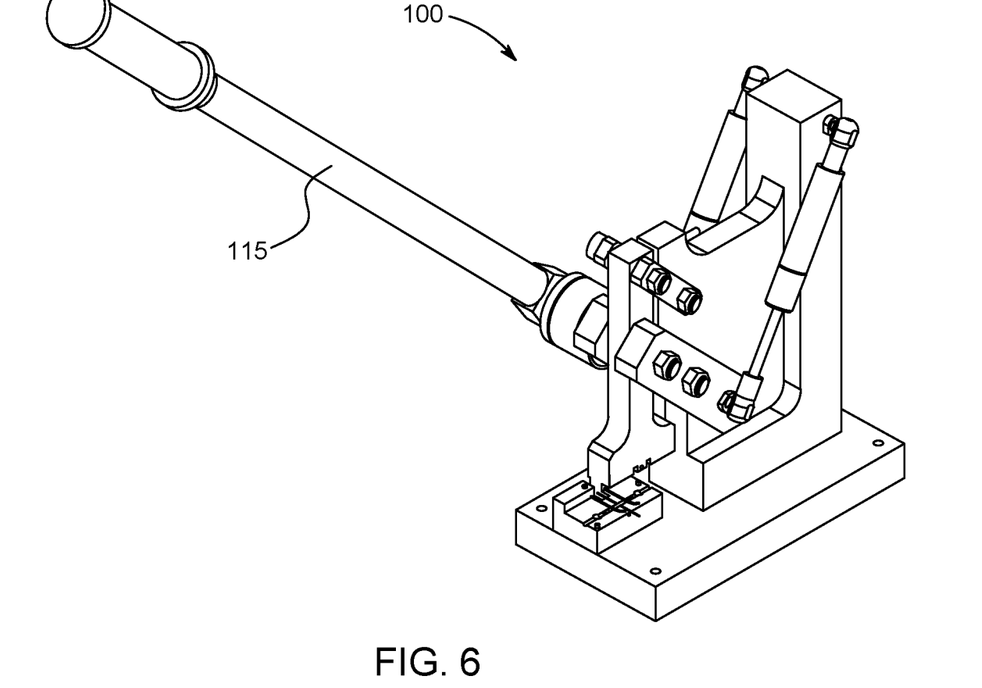
FIG. 6 is a perspective view showing a further embodiment of the presently disclosed crimping device comprising a lever and mechanisms for holding and pressing the lower and upper blocks against each other.

FIG. 6 shows a further embodiment of the presently disclosed crimping device (100) comprising a lever (115) and mechanisms for holding and pressing the lower (103) and upper blocks (104) against each other.

Figure 7:
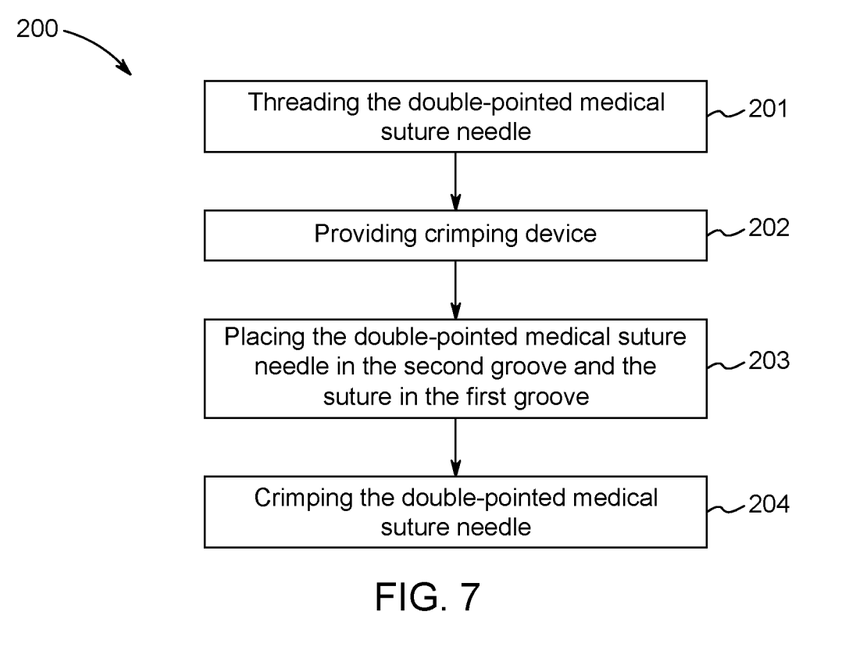
FIG. 7 is an exemplary flow chart of the presently disclosed method of securing at least one suture to at least one double-pointed medical suture needle.

FIG. 7 shows an exemplary flow chart of the presently disclosed method of securing at least one suture to at least one double-pointed medical suture needle (200). The method (200) comprises the steps of: threading the double-pointed medical suture needle by inserting the suture through a through-hole of the double-pointed medical suture needle (201); providing the presently disclosed crimping device (202)—the crimping device may, for example, comprise a lower block and an upper block, each of the lower block and the upper block comprising a first groove configured to accommodate the suture; and a second groove configured to accommodate the double-pointed medical suture needle, the second groove extending in a second groove extension substantially perpendicular to a first groove extension of the first groove, wherein the second groove comprises a protrusion at an intercept of the first groove and second groove; placing the double-pointed medical suture needle in the second groove and the suture in the first groove (203); and crimping the double-pointed medical suture needle by pressing the lower block and the upper block together, thereby securing the suture to the double-pointed medical suture needle (204).

FIG. 8 shows an embodiment of the presently disclosed crimping device (100) comprising a suture length adjustment elements (119) for adjusting the length of the suture (101) before it is cut, which can be done using a cutting mechanism (118) for cutting the suture (101). The crimping device (100) comprises a lower blocked (103) and an upper block (104) that can be pressed against other using a holding and pressing mechanism (117) and a lever (115). In the embodiment a plurality of double-pointed medical suture needles (102) can be contained in a container (116), wherein the same suture (101) can be threaded through all of the double-pointed medical suture needles (102). The container (116) in the example is primarily used for needles that have not yet been crimped. One by one the double-pointed medical suture needles (102) can then be placed in the lower block (103) and crimped by pressing the upper block (104) against the lower block (103).

LIST OF ELEMENTS IN FIGURES

100—crimping device
101—double-pointed medical suture needle
102—suture
103—lower crimping-pin
104—upper crimping pin
105—lower and upper springs
106—pointed end
107—calibration pins
108—guide pins
109—guide channels
110—second groove
111—first groove
112—lower block
113—secondary lower block
114—upper block
115—secondary upper block
116—through-hole
117—free space
118—adjustment element
119—lower crimping pin channel
120—upper crimping pin channel
121—sub-blocks
122—holder element
123—substantially flat side
124—first threads
125—second threads
126—calibration pin threads
127—gap adjustment guide
128—needle gap adjustment element
129—suture gap adjustment element
200—crimping system
201—lever
202—holding and pressing mechanism Further Details of the Invention 1. A crimping device for securing a suture to a double-pointed medical suture needle, the crimping device comprising:
    a lower block and an upper block that can be pressed towards each other to secure the suture to the double-pointed medical suture needle, the lower block comprising:
    a. a first groove configured to accommodate the suture;
    b. a second groove configured to accommodate the double-pointed medical suture needle, the second groove extending in a second groove extension substantially perpendicular to a first groove extension of the first groove, wherein the second groove comprises a protrusion at an intercept of the first groove and second groove.

2. The crimping device according to item 1, wherein the crimping device is configured to secure the suture to a double-pointed medical suture needle having a through-hole in and two indentations in a needle body, wherein the crimping device comprises at least one locking element, for example two locking elements, such as two rods, configured to engage with indentations of the double-pointed medical suture needle in a locked position such that the through-hole is aligned with the intercept.

3. The crimping device according to item 2, wherein the locking element(s) is/are disposed on a lower block needle facing surface to lock the double-pointed medical suture needle against the lower block in the locked position.

4. The crimping device according to item 3, wherein the upper block comprises locking element receiving grooves for receiving the locking elements in the locked position.

5. The crimping device according to item 2, wherein the locking element(s) is/are arranged substantially perpendicularly to a lower block needle facing surface, the locking element(s) partly interfering with the second groove.

6. The crimping device according to item 5, wherein the upper block comprises guiding holes for receiving the locking elements.

7. The crimping device according to any one of the preceding items, wherein the protrusion of each of the lower block and the upper block is a bulge.

8. The crimping device according to any one of the preceding items, wherein the protrusions cause a deformation of the double-pointed medical suture needle to bond the suture to the double-pointed medical suture needle when the lower block and the upper block are pressed against each other.

9. The crimping device according to item 8, wherein the protrusions cause a deformation of the double-pointed medical suture needle from two opposite sides.

10. The crimping device according to any one of the preceding items, wherein the first groove and the second groove are substantially straight.

11. The crimping device according to any one of the preceding items, wherein the lower block and the upper block have suture side openings for the suture.

12. The crimping device according to any one of the preceding items, wherein the lower block and the upper block have needle side openings for the double-pointed medical suture needle.

13. The crimping device according to any one of the preceding items, wherein the first groove has a first height and the second groove has a second height, wherein the second height is greater than the first height.

14. The crimping device according to item 13, wherein the second height corresponds to a needle radius of the double-pointed medical suture needle.

15. The crimping device according to any one of items 13-14, wherein the second groove has a third height at the protrusion, wherein the third height is greater than the first height and less than the second height.

16. The crimping device according to any one of the preceding items, wherein the lower block and the upper block comprise a free space around each pointed end of the double-pointed medical suture needle.

17. The crimping device according to item 16, wherein the free space is a substantially spherical space.

18. The crimping device according to any one of the preceding items, further comprising a cutting mechanism for cutting the suture.

19. The crimping device according to any one of the preceding items, further comprising a winding mechanism for winding the suture and/or one or more suture length adjustment elements.

20. A method of securing at least one suture to at least one double-pointed medical suture needle, comprising the steps of:
threading the double-pointed medical suture needle by inserting the suture through a through-hole of the double-pointed medical suture needle;
providing a crimping device having a lower block and an upper block, each of the lower block and the upper block comprising a first groove configured to accommodate the suture; and a second groove configured to accommodate the double-pointed medical suture needle, the second groove extending in a second groove extension substantially perpendicular to a first groove extension of the first groove, wherein the second groove comprises a protrusion at an intercept of the first groove and second groove;
placing the double-pointed medical suture needle in the second groove and the suture in the first groove; and
crimping the double-pointed medical suture needle by pressing the lower block and the upper block together, thereby securing the suture to the double-pointed medical suture needle.

21. The method of securing a suture to a double-pointed medical suture needle according to item 20, further comprising the step of locking the double-pointed medical suture needle by engaging one or more locking elements with one or more indentations of the double-pointed medical suture needle such that the through-hole is aligned with the intercept.

22. The method of securing a suture to a double-pointed medical suture needle according to any one of items 20-21, wherein the protrusion of each of the second groove deform the double-pointed medical suture needle at the through-hole.

23. The method of securing a suture to a double-pointed medical suture needle according to any one of items 20-22, further comprising the step of cutting the suture.

24. The method of securing a suture to a double-pointed medical suture needle according to any one of items 20-23, wherein a plurality of double-pointed medical suture needles are threaded using the same suture, and wherein the double-pointed medical suture needles are crimped one by one, wherein the suture is winded and cut for each crimping.

25. The method of securing a suture to a double-pointed medical suture needle according to any one of items 20-24, wherein the crimping device is a crimping device according to any one of items 1-19.

The invention claimed is:

1. A crimping device for securing a suture to a double-pointed medical suture needle, the crimping device comprising:
a lower block and an upper block that can be pressed against each other to secure the suture to the double-pointed medical suture needle, each of the lower block and upper block comprising:
a first groove configured to accommodate the suture; and
a second groove configured to accommodate the double-pointed medical suture needle, the first and second grooves arranged substantially perpendicularly to each other, wherein the second groove comprises a protrusion at an intercept of the first groove and second groove.

2. The crimping device according to claim 1, wherein the crimping device is configured to secure the suture to a double-pointed medical suture needle having a through-hole in and two indentations in a needle body, wherein the crimping device further comprises at least one locking element configured to engage with indentations of the double-pointed medical suture needle in a locked position such that the through-hole is aligned with the intercept.

3. The crimping device according to claim 2, wherein the locking element(s) is/are disposed on a lower block needle facing surface to lock the double-pointed medical suture needle against the lower block in the locked position.

4. The crimping device according to claim 3, the upper block further comprising locking element receiving grooves for receiving the locking elements in the locked position.

5. The crimping device according to claim 2, wherein the locking element(s) is/are arranged substantially perpendicularly to a lower block needle facing surface, the locking element(s) partly interfering with the second groove, and wherein the upper block comprises guiding holes for receiving the locking elements.

6. The crimping device according to claim 2, wherein the at least one locking element comprises two locking elements.

7. The crimping device according to claim 6, wherein the two locking elements are two rods.

8. The crimping device according to claim 1, wherein the protrusions cause a deformation of the double-pointed medical suture needle to bond the suture to the double-pointed medical suture needle when the lower block and the upper block are pressed against each other.

9. The crimping device according to claim 1, wherein the protrusions cause a deformation of the double-pointed medical suture needle from two opposite sides.

10. The crimping device according to any claim 1, wherein the first groove and the second groove are substantially straight.

11. The crimping device according to claim 1, wherein the lower block and the upper block have suture side openings for the suture.

12. The crimping device according to claim 1, wherein the first groove has a first height and the second groove has a second height, wherein the second height is greater than the first height.

13. The crimping device according to claim 12, wherein the second height corresponds to a needle radius of the double-pointed medical suture needle.

14. The crimping device according to claim 12, wherein the second groove has a third height at the protrusion, wherein the third height is greater than the first height and less than the second height.

15. A method of securing at least one suture to at least one double-pointed medical suture needle, comprising the steps of:

threading the double-pointed medical suture needle by inserting the suture through a through-hole of the double-pointed medical suture needle;

providing a crimping device having a lower block and an upper block, each of the lower block and the upper block comprising a first groove configured to accommodate the suture; and a second groove configured to accommodate the double-pointed medical suture needle, the first and second grooves arranged substantially perpendicularly to each other, wherein the second groove comprises a protrusion at an intercept of the first groove and second groove;

placing the double-pointed medical suture needle in the second groove and the suture in the first groove; and crimping the double-pointed medical suture needle by pressing the lower block and the upper block together, thereby securing the suture to the double-pointed medical suture needle.

16. The method of securing a suture to a double-pointed medical suture needle according to claim 15, further comprising the step of locking the double-pointed medical suture needle by engaging one or more locking elements with one or more indentations of the double-pointed medical suture needle such that the through-hole is aligned with the intercept.

17. The method of securing a suture to a double-pointed medical suture needle according to claim 15, wherein the protrusion of each of the second groove deform the double-pointed medical suture needle at the through-hole.

* * * * *